| United States Patent [19] | [11] | 4,100,216 |
|---|---|---|
| Myers, Jr. et al. | [45] | Jul. 11, 1978 |

[54] PREPARATION OF BETA-METHYLTETRAMETHYLENE NORTRICYCLANE

[75] Inventors: Harry K. Myers, Jr., Aston; James E. Lyons, Wallingford; Abraham Schneider, Overbrook Hills, all of Pa.

[73] Assignee: Sun Oil Company of Pennsylvania, Philadephia, Pa.

[21] Appl. No.: 819,445

[22] Filed: Jul. 27, 1977

[51] Int. Cl.$^2$ .............................................. C07C 13/32
[52] U.S. Cl. .......................... 260/666 PY; 260/666 B; 260/666 A; 44/7 R
[58] Field of Search ......... 260/666 PY, 666 B, 666 A

[56] References Cited

U.S. PATENT DOCUMENTS 2,875,256  2/1959  Hyman ............................ 260/666 A

OTHER PUBLICATIONS

A. Greco et al., J. Org. Chem., vol. 35, No. 1, pp. 271–274, 1970.

*Primary Examiner*—Veronica O'Keefe
*Attorney, Agent, or Firm*—J. Edward Hess; Donald R. Johnson; Anthony Potts, Jr.

[57] ABSTRACT

Norbornadiene and isoprene are catalytically codimerized to an olefinic codimer. Used is a three-component homogeneous catalytic system consisting of cobaltic or cobaltous acetylacetonate, 1,2-bisdiphenylphosphino ethane and an alkyl aluminum chloride. The codimer upon hydrogenation forms β-methyltetramethylene nortricyclane having utility as a diluent for a high energy hydrocarbon missile fuel.

10 Claims, No Drawings

PREPARATION OF BETA-METHYLTETRAMETHYLENE NORTRICYCLANE

BACKGROUND OF THE INVENTION

The invention herein described was made in the course of or under a contract thereunder with the United States Air Force Systems Command.

The invention relates to the catalytic codimerization of norbornadiene and isoprene (also known as 2-methyl-1,3-butadiene); the latter is hereinafter referred to as IP. Particularly the invention relates to the preparation of an olefinic codimer of norbornadiene and isoprene using a specified catalyst system. Hydrogenation of the olefinic codimer yields a saturated codimer having utility as a high energy fuel or a diluent for such fuels.

High energy fuel, which is often referred to as a high density fuel, can be used in either jet or rocket propulsion. Jet propulsion includes a jet engine which can be used for a missile plane and others and includes the three basic types, i.e., ramjet, turbo-jet and pulse jet. The term rocket generally refers to a device containing its own oxygen or oxidizing agent.

Norbornadiene is also known as bicyclo-(2.2.1) heptadiene-2,5. A method of preparation is disclosed in U.S. Pat. No. 2,875,256 issued Feb. 24, 1959. Hereinafter, norbornadiene is referred to as NBD. The latter can be represented by either one of the following structural formulas:

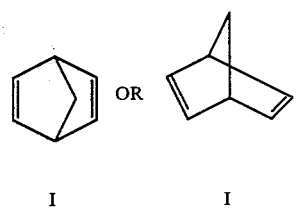

I      I

NBD can be easily dimerized to a exo-exo hexacyclic dimer. Thus one problem in reacting NBD with another hydrocarbon reactant is to minimize the formation of the foregoing dimer while encouraging the formation of the desired codimer.

A. Greco et al, in the Journal of Organic Chemistry, Vol. 35, No. 1, Jan. 1970, page 271 in an article titled "Catalytic Norbornadiene-Butadiene and Norbornadiene-1,1-Dimethylallene Codimerization" discloses using bis(cyclooctatetraene) iron or $FeCl_3$-(i-$C_3H_7$)MgCl as a catalyst for reacting NBD with IP. While reporting 1:1 adducts of the latter none were isolated because of low yields.

SUMMARY OF THE INVENTION

Rapid codimerization of NBD and IP is obtained using a catalytic amount of a three-component homogeneous catalytic system consisting of cobaltic or cobaltous acetylacetonate, 1,2-bisdiphenylphosphino ethane and one of three alkyl aluminum chlorides. The reaction rate is relatively rapid and the selectivity as to the resulting codimer of NBD and IP is good. Resulting codimer can be hydrogenated and then used as a missile fuel diluent.

DESCRIPTION

Cobaltic acetylacetonate ($Co(C_5H_7O_2)_3$) is referred to hereinafter as $CoA_3$ whereas the cobaltous form (Co($C_5H_7O_2)_2$) is referred to as $CoA_2$; collectively the two are referred to as CoA. The 1,2-bisdiphenylphosphino ethane is referred to as DIPHOS while the alkyl aluminum chloride is referred to as AAC.

The catalytic codimerization of NBD and IP via present invention can be represented by the following formula reaction:

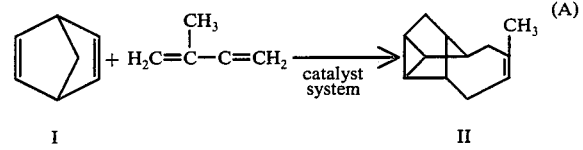

As shown, NBD and IP are contacted in the presence of a catalytic amount of the catalyst system defined herein. Coproducts may also be formed.

Olefinic codimer II is a tetracyclic hydrocarbon having the molecular formula $C_{12}H_{16}$ and a C/H molar ratio of 0.750. Codimer II, prepared as described hereinafter, with a purity of 89%, has a boiling point of 47°–48° C at 0.2 mm of Hg. Its net heating value is 149,740 BTU/gallon and its density at (d20/4) is 0.9959.

Codimer II upon hydrogenation forms $\beta$-methyltetramethylene nortricyclane III in a major amount. The hydrogenation of olefinic codimer II can be represented by the following formula reaction:

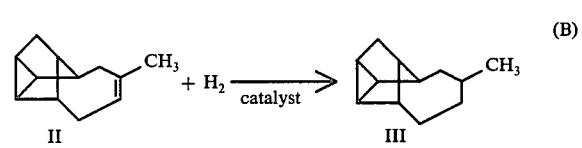

Codimer II readily hydrogenates to product III in the presence of a hydrogenation catalyst such as $PtO_2$.

Hydrogenated product III is also a tetracyclic hydrocarbon having the molecular formula $C_{12}H_{18}$ and a C/H molar ratio of 0.667. Product III, prepared as described hereinafter, at 95% purity, has a density at (d20/4) of 0.9654 and a KV at 100° F of 3.0 cst. Also the product is a clear, colorless liquid boiling at about 47°–48° C at 0.2 mm of Hg. Because of its properties it can be used as a high density diluent for mixing with missile fuel hydrocarbon components having poor low temperature viscosities.

The NBD used can contain a nominal amount of similar hydrocarbons, however, which if present should not be of a type which could adversely effect the reaction. If the NBD used contains undesirable hydrocarbons, they can be removed by known means. The foregoing also applies to the IP used. Thus the hydrocarbons used in the invention can consist essentially of NBD and IP.

In the codimerization of NBD and IP one mole of each reacts with the other to form one mole of the NBD-IP codimer II. However, if the NBD to IP mole ratio is too large homodimerization can occur with an adverse effect on codimer yields. On the other hand, if the NBD to IP mole ratio is too low then the yield per pass can be too low and hence uneconomical. Within the aforementioned range a preferred NBD to IP mole ratio is in the range between from about 0.01 to about 10 with about 0.1 to about 5 more preferred.

The catalytic system favoring the aforementioned codimerization reaction A contains three components.

All three components of the catalyst system are commercially available and methods for their preparation are reported in the literature. The three are CoA$_3$ or CoA$_2$, DIPHOS and AAC. The AAC can be selected from the group consisting of diethylaluminum chloride, ethyl aluminum dichloride and ethyl aluminum sesquichloride. The three are referred to as DEAC, EADC and EASC, respectively. The amount of any component present is a catalytic amount so that a suitable conversion to codimer II occurs and the selectivity as to it is sufficient. Material, which during the codimerization reaction could adversely affect the catalyst system, should not be present. For example, the presence of hydroxylic compounds such as water, alcohol or oxygen from air could deactivate the catalyst system.

The amount of CoA present should be catalytically sufficient to obtain the desired product. Generally the NBD to CoA mole ratio can range between from about 10 to about 2000 with a preferred range between from about 20 to about 1000.

The second component of the catalyst system is DIPHOS which has the following formula:

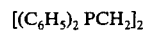

$$[(C_6H_5)_2 PCH_2]_2$$

The amount of this second component of the catalyst system should be catalytically sufficient to obtain the desired product. Generally the DIPHOS to CoA mole ratio can range between from about 0.1 to about 5 with a preferred range between from about 1 to about 4. DEAC, EADC or EASC is the third component of the catalyst system with DEAC preferred. The amount of the third component can vary substantially but generally it relates to the amount of CoA used. An effective DEAC, EADC or EASC to CoA mole ratio can be between from about 0.5 to about 100 with from about 1 to about 50 preferred and from about 3 to about 20 more preferred. Generally, when DEAC, EADC or EASC is used it is advantageous to conduct the reaction under substantially anhydrous conditions and under an inert gas blanket. Excess DEAC, EADC or EASC also serves as a scavenger.

Selectivity refers to the amount, mole or weight, of a particular compound formed divided by the amount of all compounds formed. From a commercial standpoint the economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. The catalyst to feed ratios are discussed herein while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in an inert solvent such as toluene rather than NBD itself. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, ethers, halogenated aromatics, halogenated paraffins and halogenated cycloparaffins. Specific examples include benzene, toluene, xylenes, cyclohexane, diethylether, chlorobenzene, bromobenzene, chlorinated cyclohexane and the like. As to the amount of solvent used, excessive amounts decrease the reaction rate, and thus adversely affect the economics for a commercial operation.

The codimerization of NBD and IP with the three-component catalyst system can occur at ambient temperature. Thus the temperature of the mixture of feed and homogeneous catalyst system need not be raised to initiate reaction A. However, if the mixture is at an extremely low temperature, then heating of the cooled mixture could be necessary. Furthermore, once reaction A is underway, some heat is generated and the temperature of the mixture increases. If the temperature increases too much then some cooling would be required. Generally, however, the codimerization of NBD and IP with a reasonable amount of the three-component catalyst system is not characterized by an extremely rapid exotherm.

Selective codimerization of the NBD and IP most efficiently occurs in a liquid phase and therefore it is not desirable to have the reaction temperature largely exceed the boiling points of the NBD and/or any solvent. Conversely, if the temperature is too low the reaction rate will be too slow to be economically feasible. An operable temperature range is between from about 20° C to about 100° C with about 25° C to about 85° C a preferred range. The operating pressure can vary substantially, however, it can range from about atmospheric up to about 2000 psi with about 1000 psi a preferred upper value. Process economics favor lower operating pressure, however, a moderately elevated reaction pressure may be desirable to keep the IP in solution.

To further illustrate the invention, the following examples are provided.

EXAMPLES

The accompanying Table summarizes the codimerization runs which were carried out. Analysis of the results of runs 1–3 indicate that codimer II was prepared along with some coproducts. Comparison of runs 1–3 indicate that yields as to codimer II increase with time.

The data reported in the Table were obtained in the following manner. Into a Fisher-Porter reaction vessel were added 0.712 grams (2 millimoles) of CoA$_3$, along with 1.194 grams (3 millimoles) of DIPHOS and 50 milliliters of toluene and 10 milliliters of NBD and 1 milliliter of IP. The resulting mixture was stirred, deaerated with argon and cooled to 10° C. Into a second Fisher-Porter reaction vessel were added 10 milliliters of toluene and 90 milliliters of NBD and 49 milliliters of IP. The resulting mixture was stirred, deaerated with argon at 24° C.

After both mixtures were prepared 23 milliliters of 1 molar solution of DEAC in toluene was added to the first Fisher-Porter vessel while cooling the resulting mixture down to 0° C.

The contents of the second Fisher-Porter vessel were then slowly pumped into the first vessel over an 80 minute period. The temperature of the contents of the first vessel reached about 50° C after about 50 minutes where it was maintained for the rest of the reaction in the case of run 3.

At the conclusion of the reaction period the reaction mixture was treated with aqueous HCl at 0° C to quench the catalyst. After separation, a sample of the resulting hydrocarbon mixture was analyzed by vapor phase chromatographic analysis (vpc). The results of the vpc analysis are given in the Table.

Also, the reaction product from run 2 was distilled and the cut boiling from 47°–48° C at 0.2 mm Hg was found to be 89% of codimer II.

A portion of the distilled material was hydrogenated using platinum oxide as a catalyst at 25° C and 50 psi hydrogen in a glass Parr hydrogenation apparatus. The resulting reaction mixture was filtered and the hydrogenated product III was isolated at 95% purity by vapor phase chromatography.

Both codimer II and product III were examined by infrared and NMR spectroscopy and mass spectrometry and results were consistent with assigned structures.

Attempts to obtain the melting point of product III by differential scanning calorimeter were unsuccessful. The problem was that product III, which is a mixture of two isomers, would not solidify even after chilling to −120° C and seeding with silica gel and alumina.

Similar results will be obtained if the $CoA_3$ is replaced by $CoA_2$ and/or the DEAC is replaced by EADC or EASC.

TABLE

Codimerization of NBD and IP

| Run[a] | Volume Ratio NBD to IP | Max. T, °C | Time Hrs. | Yield Dimer % | Selectivity % Co-dimer II | Hexa-Cyclics | Binor-S |
|---|---|---|---|---|---|---|---|
| 1 | 2.0 | 49 | 2.4 | 11 | 49 | 47 | 4 |
| 2 | 2.0 | 64 | 4.8 | 23 | 39 | 60 | 1 |
| 3 | 2.5 | 50 | 5.6 | 42 | 48 | 44 | 9 |

Note
[a] Catalyst system is $CoA_3$-DIPHOS-DEAC; weight ratio of $CoA_3$ to DIPHOS = 0.6; solvent is toluene.

The invention claimed is:

1. Process for the catalytic codimerization of norbornadiene and isoprene comprising:
    (a) contacting norbornadiene and isoprene in the presence of a catalytic amount of a three-component homogeneous catalytic system consisting of cobaltic or cobaltous acetylacetonate, 1,2-bisdiphenylphosphino ethane and one of the following alkyl aluminum chlorides: diethylaluminum chloride, ethyl aluminum dichloride and ethyl aluminum sesquichloride;
    (b) having the contacting occurring at a temperature within the range from between about 20° C to about 100° C; and
    (c) continuing the contacting until the desired amount of codimer of norbornadiene and isoprene is prepared.
2. Process according to claim 1 wherein the norbornadiene to the acetylacetonate mole ratio is in the range between from about 10 to about 2,000.
3. Process according to claim 1 wherein the bisdiphenylphosphino ethane to the acetylacetonate mole ratio is in the range between from about 0.1 to about 5.
4. Process according to claim 1 wherein the norbornadiene to isoprene mole ratio is in the range between from about 0.01 to about 10.
5. Process according to claim 1 wherein the alkyl aluminum chloride to the acetylacetonate mole ratio is in the range between from about 0.5 to about 100.
6. Process according to claim 5 wherein an inert solvent is present.
7. Process according to claim 6 wherein the inert solvent is selected from the group consisting of aromatic hydrocarbon, cycloparaffin, ether, halogenated aromatic, halogenated paraffin and halogenated cycloparaffin.
8. Process according to claim 7 wherein bisdiphenylphosphino ethane to acetylacetonate mole ratio is in the range between from about 0.1 to about 5.
9. Process according to claim 8 wherein the norbornadiene to isoprene mole ratio is in the range between from about 0.01 to about 10.
10. Process according to claim 9 wherein the norbornadiene to the acetylacetonate mole ratio is in the range between from about 10 to about 2,000.

* * * * *